(12) United States Patent
Suryanarayanan et al.

(10) Patent No.: US 12,062,454 B2
(45) Date of Patent: Aug. 13, 2024

(54) ARTIFICIAL INTELLIGENCE-ASSISTED NON-PHARMACEUTICAL INTERVENTION DATA CURATION

(71) Applicant: International Business Machines Corporation, Armonk, NY (US)

(72) Inventors: Parthasarathy Suryanarayanan, Croton On Hudson, NY (US); Ching-Huei Tsou, Briarcliff Manor, NY (US); Ananya Aniruddha Poddar, White Plains, NY (US); Diwakar Mahajan, New York, NY (US); Bharath Dandala, White Plains, NY (US); Divya Ranganathan Pathak, Westchester, NY (US); Piyush Madan, Boston, MA (US); Michal Rosen-Zvi, Jerusalem (IL); Aisha Walcott, Nairobi (KE)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 420 days.

(21) Appl. No.: 17/402,123

(22) Filed: Aug. 13, 2021

(65) Prior Publication Data
US 2023/0047800 A1   Feb. 16, 2023

(51) Int. Cl.
*G06F 16/40*   (2019.01)
*G06F 16/951*   (2019.01)
(Continued)

(52) U.S. Cl.
CPC ........... *G16H 50/70* (2018.01); *G06F 16/951* (2019.01); *G06F 40/30* (2020.01); *G16H 50/20* (2018.01)

(58) Field of Classification Search
None
See application file for complete search history.

(56) References Cited

U.S. PATENT DOCUMENTS

| | | |
|---|---|---|
| 7,765,574 B1 | 7/2010 | Maybury et al. |
| 9,424,524 B2 | 8/2016 | Dave et al. |

(Continued)

OTHER PUBLICATIONS

Liam G. McCoy, CAN-NPI: A Curated Open Dataset of Canadian Non-Pharmaceutical Interventions in Response to the Global COVID-19 Pandemic, Apr. 22, 2020.*

(Continued)

*Primary Examiner* — Thu N Nguyen
(74) *Attorney, Agent, or Firm* — Amin, Turocy & Watson, LLP (57) ABSTRACT

Systems, devices, computer-implemented methods, and/or computer program products that facilitate artificial intelligence (AI)-assisted curation of non-pharmaceutical intervention (NPI) data from heterogeneous data sources. In one example, a system can comprise a processor that executes computer executable components stored in memory. The computer executable components can comprise an extraction component and a change detection component. The extraction component can extract candidate non-pharmaceutical intervention (NPI) events from data associated with a defined disease. The change detection component can evaluate the candidate NPI events for inclusion in a dataset storing NPI events in a defined format.

20 Claims, 6 Drawing Sheets

(51) Int. Cl.
    G06F 40/30    (2020.01)
    G16H 50/20    (2018.01)
    G16H 50/70    (2018.01)

(56) References Cited

U.S. PATENT DOCUMENTS

| | | | | |
|---|---|---|---|---|
| 2003/0110163 A1* | 6/2003 | Chen | ............... | G06F 16/5838 |
| 2011/0093249 A1* | 4/2011 | Holmes | ............... | G16H 50/50 |
| | | | | 703/6 |
| 2013/0046558 A1* | 2/2013 | Landi | ............... | G06F 16/27 |
| | | | | 705/3 |
| 2013/0191147 A1* | 7/2013 | Harrell | ............... | G06Q 30/0211 |
| | | | | 705/2 |
| 2014/0057241 A1* | 2/2014 | Rapp | ............... | G09B 7/02 |
| | | | | 434/353 |

OTHER PUBLICATIONS

Suryanarayanan et al., "WNTRAC: AI Assisted Tracking of Non-pharmaceutical Interventions Implemented Worldwide for COVID-19," arXiv:2009.07057v3 [cs.CY] Dec. 5, 2020, 15 pages.

McCoy et al.," CAN-NPI: A Curated Open Dataset of Canadian Non-Pharmaceutical Interventions in Response to the Global COVID-19 Pandemic," medRxiv preprint doi: https://doi.org/10.1101/2020.04.17.20068460, 2020, 21 pages.

Walcott et al., "AI Data Tracker Encourages Scientific Research into COVID-19 Non-Pharmaceutical Interventions," IBM Research Blog, Sep. 29, 2020, 9 pages.

Miikkulainen et al., "From Prediction to Prescription: AI-Based Optimization of Non-Pharmaceutical Interventions for the COVID-19 Pandemic," arXiv:2005.13766v1 [cs.NE] May 28, 2020, 35 pages.

Shuja et al., "COVID-19 open source data sets: a comprehensive survey," Applied Intelligence, Sep. 2020, 31 pages.

Imai et al., "Adoption and impact of non-pharmaceutical interventions for COVID-19," Welcome Open Research, 5:59, Jun. 1, 2020, 17 pages.

Suryanarayanan et al., "AI-assisted tracking of worldwide non-pharmaceutical interventions for COVID-19," Scientific Data 8, Article No. 94 (2021), 34 pages.

"Worldwide Non-pharmaceutical Interventions Tracker for COVID-19 (WNTRAC), " https://github.com/IBM/wntrac#start-of-content, accessed May 17, 2021, 2 pages.

"ACE (Automatic Content Extraction) English Annotation Guidelines for Entities," Linguistic Data Consortium, Version 6.6 Jun. 13, 2008, Facilities, 2008, 72 pages.

Hogenboom et al., "Financial Events Recognition in Web News for Algorithmic Trading," Lecture Notes in Computer Science (including subseries Lecture Notes in Artificial Intelligence and Lecture Notes in Bioinformatics). 2012, 10 pages.

Yakushiji et al., "Event Extraction From Biomedical Papers Using a Full Parser," Pacific Symposium on Biocomputing. Pacific Symposium on Biocomputing, Feb. 2021, 12 pages.

Tang et al., "A hybrid system for temporal information extraction from clinical text," J Am Med Informatics Assoc., 2013, 10 pages.

Piskorski et al., "Online News Event Extraction for Global Crisis Surveillance," Lect Notes Comput Sci (including Subser Lect Notes Artif Intell Lect Notes Bioinformatics), 2011, 31 pages.

Bitters, "Geospatial Reasoning in a Natural Language Processing (NLP) Environment," Proceedings of the 25th International Cartographic Conference, CO. 2011, 8 pages.

Hogenboom et al., "A Survey of Event Extraction from Text," IIEEE Access 7 (2019), 32 pages.

Xiang et al., "A Survey of Event Extraction from Text," IEEE Access 7 (2019), 29 pages.

Han et al., "Active learning for ontological event extraction incorporating named entity recognition and unknown word handling," Journal of Biomedical Semantics vol. 7, Article No. 22 (2016), 18 pages.

Cao et al., "Improving Event Detection with Active Learning," International Conference Recent Advances in Natural Language Processing, RANLP, 2015, 6 pages.

Wang et al., "A Case Study on Active Learning for Event Extraction," Chinese National Conference on Social Media Processing, 2016, 9 pages.

Hale et al., "COVID-19 Government Response Tracker," https://www.bsg.ox.ac.uk/research/research-projects/covid-19-government-response-tracker, Blavatnik School of Government, accessed Jun. 25, 2021, 17 pages.

Porcher et al., "Governments' Responses to COVID-19," https://www.openicpsr.org/openicpsr/project/119061/version/V2/view, accessed Jun. 25, 2021, 4 pages.

Chen et al., "Scenario analysis of non-pharmaceutical interventions on global COVID-19 transmissions," arXiv:2004.04529v3 [q-bio.PE] Jun. 4, 2021, 22 pages.

Wong et al., "Evaluation on different non-pharmaceutical interventions during COVID-19 pandemic: an analysis of 139 countries," The Journal of Infection (2020), 8 pages.

Flaxman et al., "Estimating the effects of non-pharmaceutical interventions on COVID-19 in Europe," Nature (2020): 1-5, 15 pages.

Hogenboom et al., "A Survey of Event Extraction Methods from Text for Decision Support Systems," Decision Support Systems 85 (2016): 12-22, 32 pages.

Rjrostron, "COVID-19 Pandemic in Hong Kong", Wikipedia, online available at <https://en.wikipedia.org/w/index.php?title=COVID-19_pandemic_in_Hong_kong&oldid=973812323>, Aug. 19, 2020, 27 pages.

* cited by examiner

ARTIFICIAL INTELLIGENCE-ASSISTED NON-PHARMACEUTICAL INTERVENTION DATA CURATION

BACKGROUND

One or more embodiments herein relate to computing devices, and more specifically, to systems, devices, computer-implemented methods, and/or computer program products that facilitate artificial intelligence (AI)-assisted curation of non-pharmaceutical intervention (NPI) data from heterogeneous data sources.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, systems, devices, computer-implemented methods, and/or computer program products that facilitate artificial intelligence (AI)-assisted curation of non-pharmaceutical intervention (NPI) data from heterogeneous data sources are described.

According to an embodiment, a system can comprise a processor that executes computer executable components stored in memory. The computer executable components can comprise an extraction component and a change detection component. The extraction component can extract candidate NPI events from data associated with a defined disease. The change detection component can evaluate the candidate NPI events for inclusion in a dataset storing NPI events in a defined format.

According to another embodiment, a computer-implemented method can comprise extracting, by a system operatively coupled to a processor, candidate NPI events from data associated with a defined disease. The computer-implemented method can further comprise evaluating, by the system, the candidate NPI events for inclusion in a dataset storing NPI events in a defined format.

According to another embodiment, a computer program product can comprise a computer readable storage medium having program instructions embodied therewith. The program instructions are executable by a processor to cause the processor to perform operations. The operations can include extracting, by the processor, candidate NPI events from data associated with a defined disease. The operations can further include evaluating, by the processor, the candidate NPI events for inclusion in a dataset storing NPI events in a defined format.

DETAILED DESCRIPTION

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Figure 1:
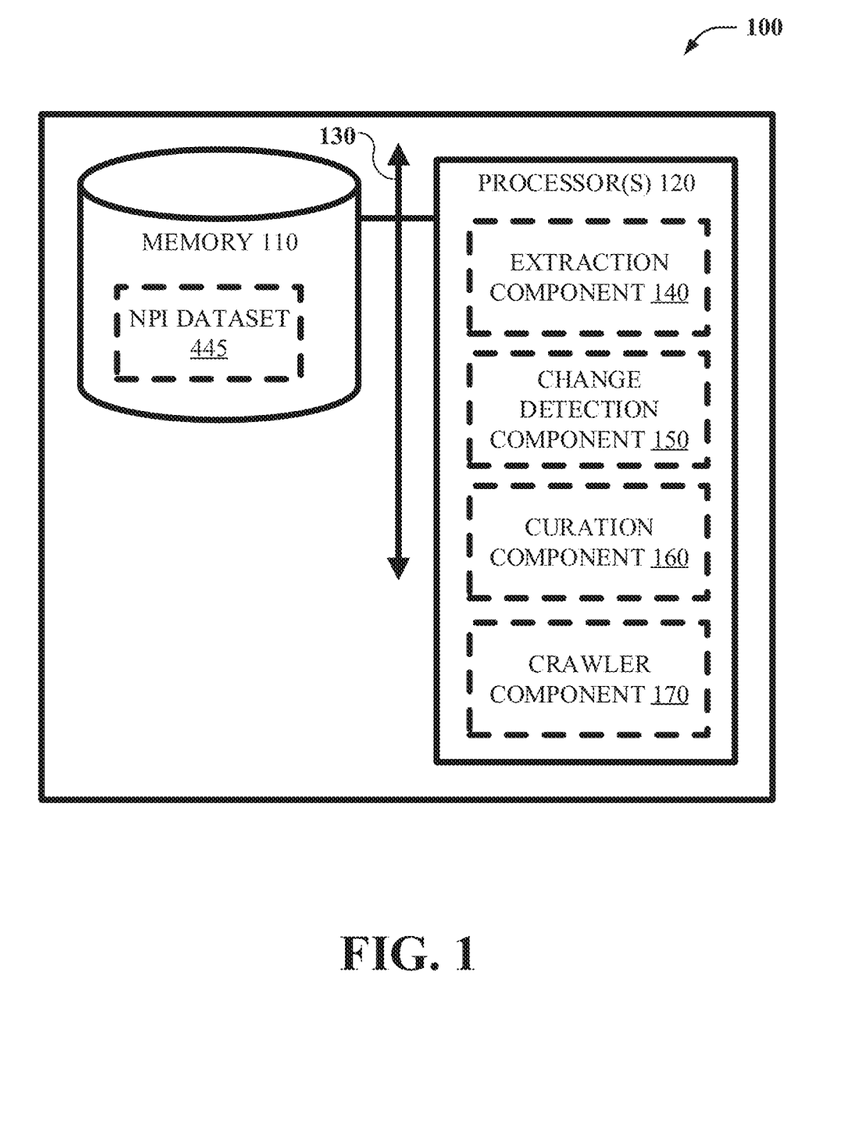
FIG. 1 illustrates a block diagram of an example, non-limiting system that can facilitate artificial intelligence (AI)-assisted curation of non-pharmaceutical intervention (NPI) data from heterogeneous data sources, in accordance with one or more embodiments described herein.

FIG. 1 illustrates a block diagram of an example, non-limiting system 100 that can facilitate artificial intelligence (AI)-assisted curation of non-pharmaceutical intervention (NPI) data from heterogeneous data sources, in accordance with one or more embodiments described herein. System 100 includes memory 110 for storing computer-executable components and one or more processors 120 operably coupled via one or more communication busses 130 to memory 110 for executing the computer-executable components stored in memory 110. As shown in FIG. 1, the computer-executable components include extraction component 140 and change detection component 150.

Extraction component 140 can extract candidate non-pharmaceutical intervention (NPI) events from data associated with a defined disease. In an embodiment, the data can be textual data of documents associated with the defined disease. In an embodiment, extraction component 140 can extract the candidate NPI events from the textual data using a natural language processing (NPL) model, as discussed in greater detail below with respect to FIG. 4. In an embodiment, extraction component 140 can extract the candidate NPI events using a sentence boundary detection algorithm to partition the textual data of the documents into sentences, as discussed in greater detail below with respect to FIG. 5.

Figure 5:
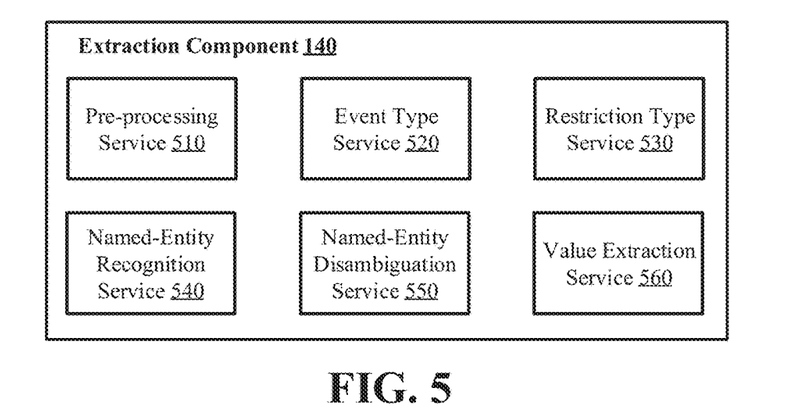
FIG. 5 illustrates an example, non-limiting application of NPI event extraction, in accordance with one or more embodiments described herein.

In an embodiment, extraction component 140 can further categorize a particular candidate NPI event among the candidate NPI events by assigning an event type of a set of event types to a given sentence of documents associated with the defined disease using a sentence classification model, as discussed in greater detail below with respect to FIG. 5. In an embodiment, extraction component 140 can further identify attributes of the candidate NPI events by evaluating textual data of documents associated with the defined disease using a named-entity recognition service and/or a named-entity disambiguation service, as discussed in greater detail below with respect to FIG. 5.

In an embodiment, extraction component 140 can further extract values for attributes of the candidate NPI events by evaluating textual data of documents associated with the defined disease using a parse-based rule algorithm, as discussed in greater detail below with respect to FIG. 5. In an embodiment, the parse-based rule algorithm can output the values for the attributes of the candidate NPI events using a result obtained from a sentence classification model, a named-entity recognition service, and/or a named-entity disambiguation service. In an embodiment, the parse-based rule algorithm can output the values for the attributes of the candidate NPI events independent of results obtained from a sentence classification model, a named-entity recognition service, and/or a named-entity disambiguation service.

Change detection component 150 can evaluate the candidate NPI events for inclusion in a dataset (e.g., NPI dataset 445) storing NPI events in a defined format. In an embodiment, the defined format the defined format can comprise a 5-tuple representation that includes a what attribute, a value attribute, a where attribute, a when attribute, and a restriction attribute, as discussed in greater detail below with respect to FIG. 5. In an embodiment, change detection component 150 can evaluate the candidate NPI events for inclusion in the dataset using similarity metrics derived from attributes of the candidate NPI events, as discussed in greater detail below with respect to FIG. 4. In an embodiment, change detection component 150 can exclude a particular candidate NPI event of the candidate NPI events from inclusion in the dataset when a corresponding similarity metric indicates the particular candidate NPI event is duplicative.

In an embodiment, system 100 can further include curation component 160 and/or crawler component 170. Curation component 160 can select a subset of NPI events stored in the structured dataset for validation using a machine learning model and/or confidence scores associated with the NPI events, as discussed in greater detail below with respect to FIG. 4. In an embodiment, curation component 160 can iteratively train the machine learning model using change data generated from validation of the subset of the NPI events stored in the dataset. Crawler component 170 can periodically crawl heterogeneous data sources (e.g., heterogeneous data sources 420 of FIG. 4) to retrieve documents associated with the defined disease. The functionality of the computer-executable components utilized by the embodiments will be covered in greater detail below.

Figure 2:
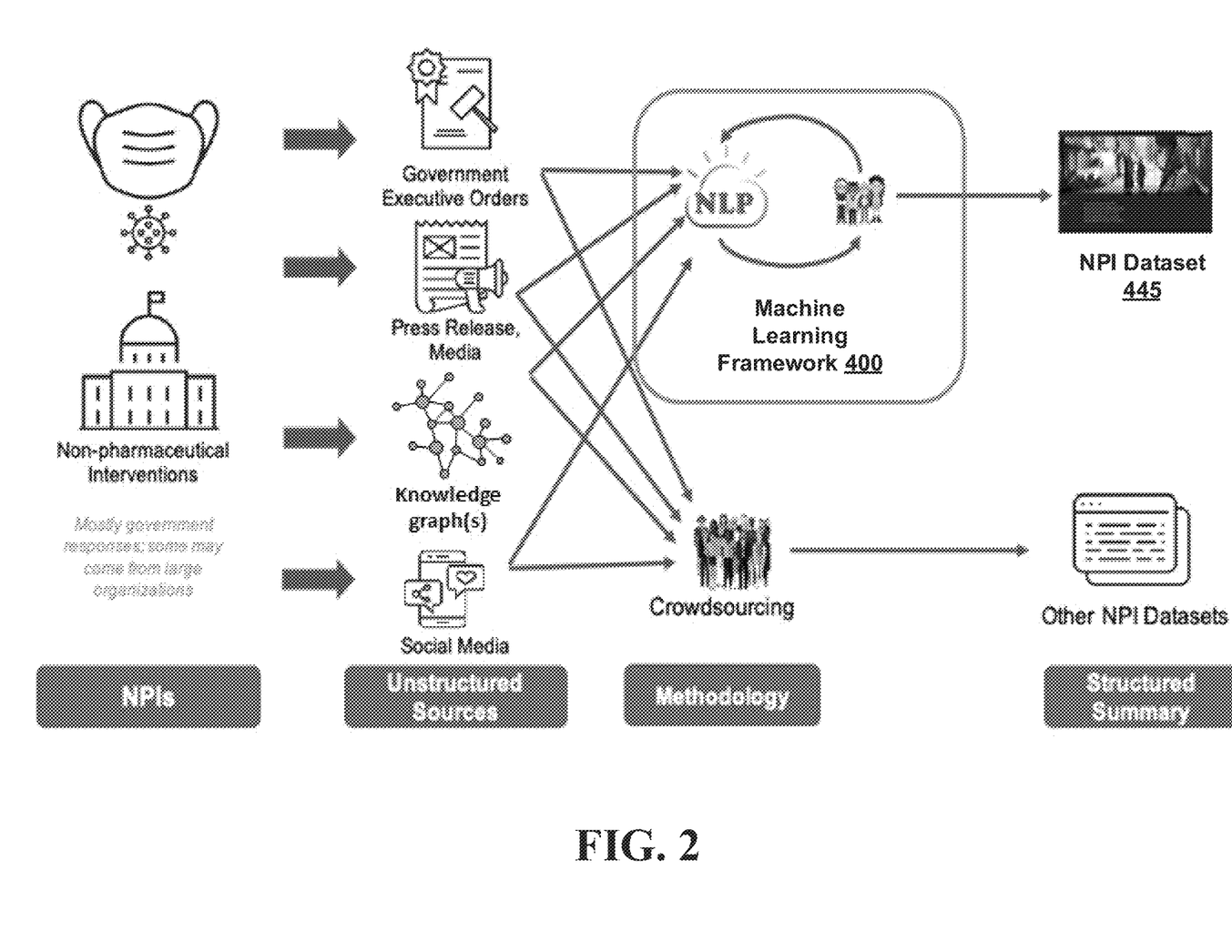
FIG. 2 illustrates an example, non-limiting high-level conceptual overview of curating NPI datasets from heterogeneous data sources.

FIG. 2 illustrates an example, non-limiting high-level conceptual overview of curating NPI data from heterogeneous data sources. The United States Centers for Disease Control and Prevention (CDC) states that NPIs can denote "actions, apart from getting vaccinated and taking medicine, that people and communities can take to help slow the spread of illnesses like the flu". Such actions can generally be implemented when vaccines or other pharmaceutical measures not yet available. Example NPIs can include, but not be limited to, community actions (e.g., school closures, restrictions on mass gatherings, and/or other community actions), individual actions (e.g., self-quarantining, and/or other individual actions), environmental actions (e.g., public facility cleaning, public transport cleaning, and/or other environmental actions), and/or other NPI-related actions.

While implementing NPIs can facilitate mitigating the spread of disease or illness, prolonged implementation of NPIs can adversely impact socio-economic public well-being. Public health policy makers worldwide strive to effectively manage disease control with NPIs while balancing any potential adverse socio-economic impact. To that end, public health policy makers generally conduct and support research to ensure that NPI-related guidance and/or recommendations are based on scientific evidence. By way of example, the Coronavirus disease 2019 (COVID-19) disease has sparked an ongoing surge of discovery and information sharing. One aspect of that ongoing surge is an unprecedented volume of data associated with COVID-19 has been generated and published online as unstructured data on a wide variety of heterogeneous data sources. That data can include information about NPIs implemented by governments and/or large organizations to mitigate the spread of COVID-19.

Public health policy makers can utilize such information to train machine learning models that predict the efficacy of implementing different NPI strategies. One challenge associated with training such machine learning models can involve curating data regarding the implementation of NPIs implemented to mitigate the spread of COVID-19 in a defined (e.g., standardized and/or structured) format. However, such NPI data is generally published as unstructured data on a wide variety of heterogeneous data sources. FIG. 2 shows that such heterogeneous data sources can include, but not be limited to: government sources, press releases or news articles, curated knowledge graphs (e.g., curated knowledge graphs underlying the Wikipedia® articles published by Wikimedia Foundation, Inc., of San Francisco, California), social media platforms, and/or other heterogeneous data sources comprising NPI-related information.

A number of data curation initiatives have emerged to create datasets that present NPI data in standardized or structured formats. While effective, these data curation initiatives generally use labor-intensive and/or time-consuming crowdsourcing methodologies to create those other NPI datasets shown by FIG. 2. Moreover, those other NPI datasets can present NPI data with varying degrees of coverage, data freshness, and/or granularity of details given the unprecedented volume of data available in the wide variety of heterogeneous data sources. Any combination of scarcity, sparsity, and/or staleness in training data can reduce the accuracy of machine learning models trained on such training data. Therefore, the varying degrees of coverage, data freshness, and/or granularity of details regarding NPI data presented by those other NPI datasets can inhibit the ability of machine learning models trained on such NPI data to predict the efficacy of implementing different NPI strategies.

As shown by FIG. 2, implementations of the present disclosure can involve a machine learning framework 400 that can facilitate AI-assisted curation of NPI data from heterogeneous data sources. Embodiments of machine learning framework 400 can facilitate creating NPI datasets (e.g., NPI dataset 445) that present such NPI data in a defined format. That defined format can facilitate mitigating the data scarcity and/or sparsity issues discussed above with respect to the other NPI datasets. Moreover, embodiments of machine learning framework 400 can continuously curate NPI data from the heterogeneous data sources to facilitate capturing incremental changes in such NPI data. Continuously curating the NPI data can facilitate mitigating the data staleness issue discussed above with respect to the other NPI datasets. Through the defined format and/or such continuous curation, embodiments of machine learning framework 400 can create NPI datasets that present robust and/or frequently updated NPI data to facilitate training machine learning models with improved predictive performance.

To facilitate presenting NPI data in a defined format, one or more embodiments of the present disclosure can model NPIs as events and evidences for information extraction purposes. In the context of NPIs, an NPI event can generally denote, but is not limited to, the imposition or lifting of a particular NPI. By way of example and with reference to FIG. 3, an NPI event can be defined using a 5-tuple representation. In this example, the 5-tuple representation defining NPI event can include a what attribute, a value attribute, a where attribute, a when attribute, and a restriction attribute.

A what attribute can denote, but is not limited to, an event type or a type of NPI that was imposed or lifted. A value attribute can denote, but is not limited to, a sub-category or attribute that can further qualify an associated event type. In an embodiment, a value attribute can facilitate fine-grained typing of an event. By way of example, "Entertainment/ Cultural Sector Closures" can be an event type and "Bars, restaurants, night clubs"—a specific type of "Entertainment/ Cultural Sector Closure" can be a corresponding value attribute. A where attribute can denote, but is not limited to, a longitudinal position, a latitudinal position, a defined landmark, and/or a geographical region (e.g., a country, a territory, a province, a state, or another geographical region) in which the NPI has been imposed or lifted. A when attribute can denote, but is not limited to, an effective date on which the NPI is imposed or lifted. A restriction attribute can denote, but is not limited to, a flag or other indication that designates the NPI event as corresponding to the imposition or lifting of the NPI. Of note, an NPI event defining the lifting of a particular NPI can be treated as separate and/or distinct from an NPI event defining the imposition of the particular NPI.

Figure 3:
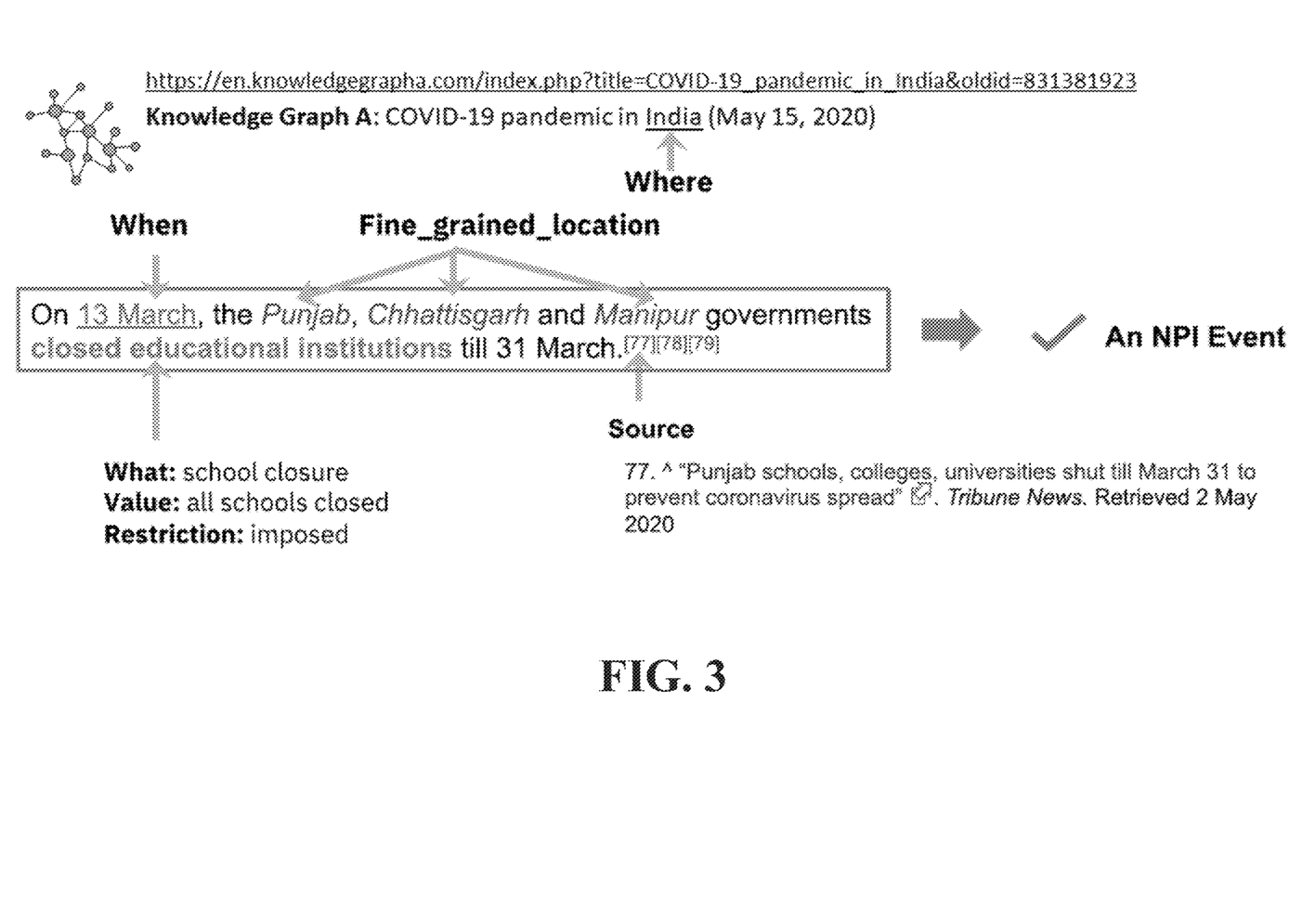
FIG. 3 illustrates an example, non-limiting machine learning framework that can facilitate AI-assisted curation of NPI data from heterogeneous data sources, in accordance with one or more embodiments described herein.

In FIG. 3, the NPI event can be defined using a 5-tuple representation comprising: (i) a what attribute that denotes a "school closure" event type as a corresponding NPI being implemented or lifted; (ii) a value attribute that further qualifies the "school closure" event type as an "all schools closed" event type; (iii) a where attribute that denotes a country in southern Asia as the geographical region in which the corresponding NPI is being implemented or lifted; (iv) a when attribute that denotes March 13th as an effective date on which the corresponding NPI was imposed or lifted; and/or (v) a restriction attribute that denotes a flag or other indication that designates the NPI event of FIG. 3 as corresponding to the imposition of the corresponding NPI. The present disclosure describes NPI events as being defined by 5-tuple representation for ease of explanation. One or more embodiments can define NPI events using an n-tuple representation where n can denote a number lower than 5 (e.g., 4) or a number higher than 5 (e.g., 6). By way of example, one or more embodiments can define an NPI event using a 6-tuple representation that comprises an attribute that denotes an enforcing body (e.g., a federal/state/local/ foreign enforcement authority, a government investigative authority, and/or other enforcing bodies) that implements and/or enforces a corresponding NPI event.

In addition to comprising a defined format (e.g., a 5-tuple representation), an NPI event can further comprise an evidence. An evidence generally denotes, but is not limited to, an instance of a data associated with a defined disease from which a given NPI event was extracted. In an embodiment, an evidence can be textual data of a document from which a given NPI event was extracted. In an embodiment, the textual data can comprise a sentence of the document. By way of example, the evidence of the NPI event shown in FIG. 3 can be the textual data comprising the sentence: "On 13 March, the Punjab, Chhattisgarh, and Manipur governments closed educational institutions till 31 March."

In an embodiment, textual data comprising evidence can be associated with citation data that can denote, but is not limited to, a source that a document references to support an assertion that an NPI was imposed or lifted. In an embodiment, the citation data can be obtained from a heterogeneous source when the document comprising the associated textual data is retrieved from the heterogeneous source. By way of example, the citation data associated with the evidence in FIG. 3 can denote the news article retrieved 2 May 2020. In an embodiment, an NPI event can comprise an additional attribute that further qualifies a particular attribute of a 5-tuple representation that defines the NPI event. By way of example, the NPI event of FIG. 3 comprises three fine-grained location attributes (e.g., fine-grained location attributes that denote the Punjab, Chhattisgarh, and Manipur states of the country in southern Asia) that further qualify the where attribute of the 5-tuple representation defining that NPI event.

A taxonomy of NPI dataset 445 can comprise a set of event types. For example, the set of event types can include, but not be limited to, a domestic flight restriction event type, a contact tracing event type, an economic impact event type, an international flight restriction event type, a protective gear event type, a school closure event type, a gathering restriction event type, a tourist quarantine event type, a public service closure event type, a state of emergency event type, a public transportation event type, and/or other event types. In an embodiment, the set of event types comprising the taxonomy of NPI dataset 445 can include 16-event types. In an embodiment, machine learning framework 400 can assign a specific event type comprising a set of event types to a particular NPI event to facilitate categorizing NPI events, as discussed in greater detail below with respect to FIG. 5.

As discussed above, a value attribute can further qualify a particular event type of the set of event types. For example, a value attribute associated with a domestic flight restriction event type can denote a particular state within a country to which the domestic flight restriction event type applies. As another example, a value attribute associated with a school closure event type can denote that all schools are closed by a corresponding NPI and/or a particular subset of schools (e.g., only kindergartens, daycares, primary schools, secondary schools, and/or universities) are closed by that NPI. In an embodiment, value attributes can comprise various formats. For example, a value attribute can comprise an integer format, a string format, and/or a categorical format.

Figure 4:
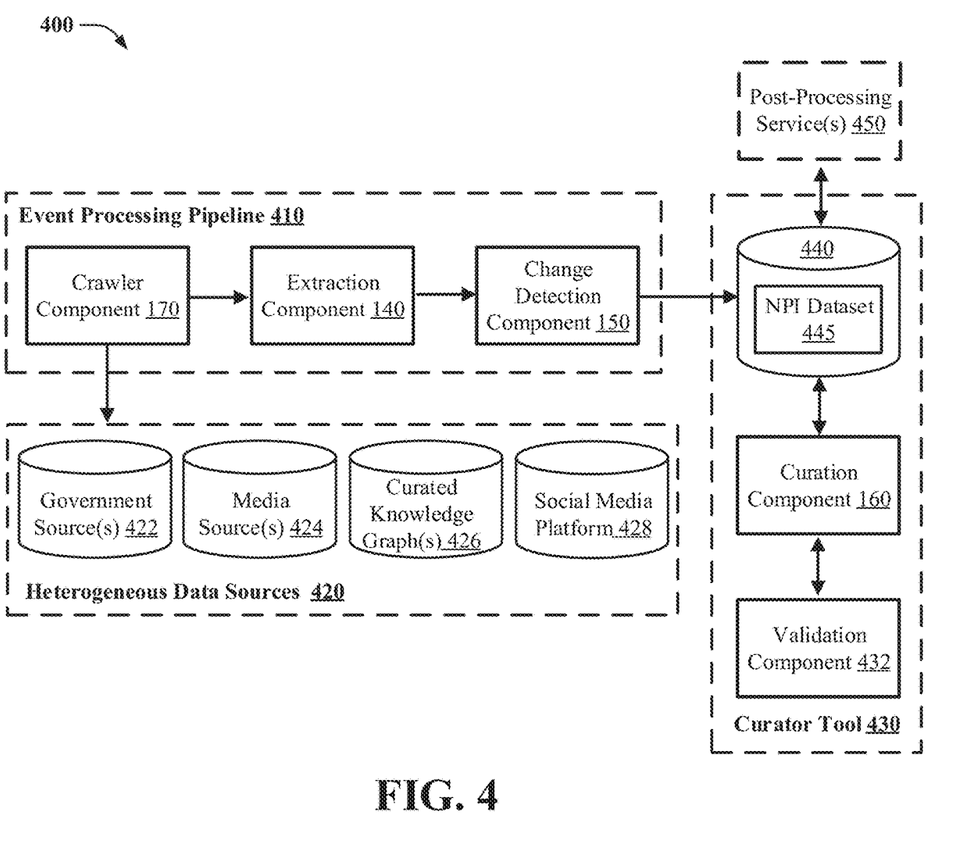
FIG. 4 illustrates an example, non-limiting architecture to implement an extraction component, in accordance with one or more embodiments described herein.

FIG. 4 illustrates an example, non-limiting architecture for implementing machine learning framework 400, in accordance with one or more embodiments described herein. As shown by FIG. 4, machine learning framework 400 can include an event processing pipeline 410 that can automatically capture NPI data from heterogeneous data sources 420 and/or extract NPI events from such data. To that end, event processing pipeline 410 can comprise crawler component 170, extraction component 140, and/or change detection component 150.

Automatically capturing NPI data from heterogeneous data sources 420 can comprise crawler component 170 identifying data associated with a defined disease (e.g., COVID-19) stored on one or more heterogeneous data sources 420, such as government sources 422, media sources 424, curated knowledge graphs 426, and/or social media platforms 428. Crawler component 170 can periodically crawl the one or more heterogeneous data sources 420 to retrieve documents associated with the defined disease. In an embodiment, crawler component 170 can retrieve the documents associated with the defined disease by downloading textual data comprising such documents from the one or more heterogeneous data sources 420. In an embodiment, crawler component 170 can further retain any citation data associated with the textual data while downloading the textual data. Crawler component 170 can output the data associated with the defined disease (e.g., NPI data automatically captured from heterogeneous data sources 420) to extraction component 140 for further processing.

In an embodiment, crawler component 170 can comprise a list of network addresses (e.g., uniform resource locators) that can define storage locations associated with the documents on the one or more heterogeneous data sources 420. In an embodiment, crawler component 170 can retrieve the documents from a given heterogeneous data source of the one or more heterogeneous data sources 420 using an application programming interface (API) associated with that heterogeneous data source. By way of example, the documents associated with the defined disease can comprise one or more Wikipedia® articles (at http://www.wikipedia.org/) a registered trademark of Wikimedia Foundation, Inc., San Francisco California. In this embodiment, crawler component 170 can retrieve the one or more Wikipedia® articles using the MediaWiki API available from Wikimedia Foundation, Inc. In an embodiment, crawler component 170 can comprise a cognitive news discovery service that can facilitate tracking news data associated with the defined disease that can be stored on media sources 324.

Extraction component 140 can extract candidate NPI events from data output by crawler component 170. To that end, extraction component 140 can comprise pre-processing service 510, event type service 520, restriction type service 530, named-entity recognition service 540, named-entity disambiguation service 550, and/or value extraction service 560, as shown by FIG. 5. In an embodiment, the data output by crawler component 170 can be textual data of documents associated with a defined disease. In an embodiment, the extraction component 140 can extract the candidate NPI events from the textual data using a NPL model.

Pre-processing service 510 can partition textual data of documents associated with a defined disease into sentences using a sentence boundary detection algorithm (e.g., a sentence boundary detection algorithm from libraries, such as NLTK, spaCy, and/or other natural language processing libraries). In an embodiment, the sentence boundary detection algorithm can partition the textual data into sentences using a transition-based dependency parser component. The transition-based dependency parser component can utilize a state machine that can define possible transitions to create a mapping from input sentences to dependency trees. The transition-based dependency parser component can comprise a machine learning model that can jointly learn sentence segmentation and/or dependency parsing using manually labelled parse trees (e.g., parse trees comprising the Treebank and/or OntoNotes datasets). In an embodiment, transition-based dependency parser component can comprise one or more aspects of the non-monotonic arc-eager transition-system described in the article "An improved non-monotonic transition system for dependency parsing" by Matthew H. et al. (2015). In this embodiment, the non-monotonic arc-eager transition-system can comprise a "break" transition to perform the sentence boundary detection along with the parsing. In an embodiment, the sentence boundary detection algorithm can partition the textual data into sentences by identifying transition points of the sentences. By way of example, the sentence boundary detection algorithm can detect a transition point of a given sentence that denotes where that sentence begins and/or a transition point of the given sentence that denotes where that sentence ends. In an embodiment, pre-processing service 510 can further preserve an order in which the sentences appear in a given document. In an embodiment, pre-processing service 510 can further extract citation data for a given sentence from the textual data.

Event type service 520 can assign classifications to sentences output by pre-processing service 510 using a first classification model. Event type service 520 can assign a discard classification to a given sentence of the sentences provided as input to the first classification model when an output of the first classification model indicates that the given sentence lacks information regarding an NPI. In an embodiment, sentences assigned the discard classification can be filtered by event type service 520 from further evaluation by other services of extraction component 140 to facilitate a reduction in computing resource consumption by extraction component 140.

Event type service 520 can assign event types to sentences output by pre-processing service 510 using a first classification model. The first classification model can utilize a small set of manually labelled sentences with associated event types. Further, the sentences output by pre-processing service 510 that do not mention any events can be labelled as "Discard". Such dataset can be used to train a machine learning model to obtain better final prediction of event types. Using this ensemble classification model, the sentences output by pre-processing service 510 can be classified into one of the NPI event types, such as school closure, to identify potential NPI events. If an NPI is not discussed in the sentence, the first classification model (e.g., an ensemble classification model) can classify it as "Discard". Event type service 520 can assign the classification denoting the particular event type when an output of the first classification model indicates that the given sentence comprises information related to the particular event type. In an embodiment, assigning classifications denoting particular event types to sentences can facilitate categorizing candidate events output by extraction component 140. In an embodiment, event type service 520 can populate a what attribute of a 5-tuple representation defining a candidate NPI event extracted from textual data comprising the given sentence based on a classification assigned by the first classification model.

By way of example, the sentence corresponding the evidence of the NPI event shown in FIG. 3 can be provided as input to the first classification model. Responsive to that input, the first classification model can generate an output indicating that sentence corresponding to the NPI event of FIG. 3 comprises information relating to a "school closure" event type. Based on that output, event type service 520 can assign a classification denoting the "school closure" event type to that sentence of FIG. 3. In this example, event type service 520 can populate a what attribute of the 5-tuple representation defining the NPI event of FIG. 3 with the "school closure" event type based on the assigned classification.

Restriction type service 530 can assign restriction classifications to sentences output by event type service 520 using a second classification model. In an embodiment, the sentences output by event type service 520 can exclude a subset of sentence output by pre-processing service 510 to which event type service 520 assigned a discard classification. Restriction type service 530 can utilize a second classification model to assign a restriction classification that can signify imposition or lifting of a particular NPI mentioned in sentence. The second classification model can utilize a small set of manually labelled dataset with "restriction imposed" or "restricted lifted" annotated on each of sentences. Such dataset can be used to train a machine learning model to obtain better final prediction of restriction type. Using the second classification model, the sentences output by event type service 520 can be classified into either "restriction imposed" or "restricted lifted" indicating that the given sentence comprises information related to the lifting or imposing of an NPI. In an embodiment, restriction type service 530 can populate a restriction attribute of a 5-tuple representation defining a candidate NPI event extracted from textual data comprising a given sentence based on the assigned restriction classification.

By way of example, the sentence corresponding to the evidence of the NPI event shown in FIG. 3 can be provided as input to the second classification model. Responsive to that input, the second classification model can generate an output indicating that sentence corresponding to the NPI event of FIG. 3 comprises information related to the imposition of an NPI. Based on that output, restriction type service 530 can a restriction classification that signifies imposition of an NPI to that sentence of FIG. 3. In this example, restriction type service 530 can populate a restriction attribute of the 5-tuple representation defining the NPI event of FIG. 3 with a flag or other indication that designates that NPI event as corresponding to the imposition of an NPI based on the assigned restriction classification.

In an embodiment, the first classification model and/or the second classification model can be a sentence classification model. In an embodiment, the first classification model and/or the second classification model can be trained using a supervised machine learning techniques and training data that comprises a subset of textual data that crawler component 170 retrieves from one or more heterogeneous data sources 420. In an embodiment, the first classification model and/or the second classification model can comprise, a logistic regression model, a support-vector machine model, a Bidirectional Encoder Representations from Transformers (BERT) model, and/or other classification models. In an embodiment, the first classification model and/or the second classification model can comprise multiple models implemented using an ensemble method. Example ensemble methods can include, but are not limited to, a bootstrap aggregating ensemble method, a boosting ensemble method, and/or other ensemble methods.

Named-entity recognition service 540 can evaluate textual data of a given document corresponding to sentences output by event type service 520 and/or restriction type service 530 to locate named entities within the textual data. Named-entity recognition service 540 can further classify the named entities into defined categories (e.g., names of persons). A named-entity tag denoting a particular entity type can be assigned to a given named entity by named-entity recognition service 540 based on such classification. Example entity types can include, but are not limited to, a Geo-Political Entity (GPE) entity type, a State-or-Providence (SoP) entity subtype, a Date entity type, and/or other entity types. Named entity recognition can typically be addressed by assigning each word BIO (Begin, Inside, and Outside) labels indicating a token's position within an entity mention as well as its type. Manually labelled datasets such as CONLL-2003 dataset can be used to train machine learning models that can utilize sequential models such as Conditional random fields, recurrent neural networks or transformed based models such as BERT. In an embodiment, named-entity recognition service 540 can comprise a bert-base-NER, a fine-tuned BERT model that is ready to use for Named Entity Recognition. This model can be trained using OntoNotes 5.0 to recognize 18 types of named entities (Person, Organization, Location, Date) and can facilitate achieving improved performance for the NER task.

Named-entity disambiguation service 550 can assign unique identities to named-entities comprising named-entity tags assigned by named-entity recognition service 540 using a named entity linking system (e.g., the ELDEN named entity linking system). Entity Linking (EL) can denote the task of mapping mentions of an entity in text to the corresponding entity in Knowledge Graph (KG). A named entity linking system (e.g., ELDEN) can first densifies the KG with co-occurrence statistics from a large text corpus, and then can use the densified KG to train entity embeddings. Entity similarity can be measured using these trained entity embeddings and the mention embeddings obtained using local contextual information. In an embodiment, named-entity disambiguation service 550 can link named-entities comprising named-entity tags denoting a GPE entity type and/or a SoP entity subtype to corresponding International Organization for Standardization (ISO) codes (e.g., using ISO 3166-1 and/or ISO 3166-2 coding). In an embodiment, named-entity disambiguation service 550 can populate a where attribute of a 5-tuple representation defining a candidate NPI event extracted from textual data comprising a given document with named-entities comprising unique identities and named-entity tags denoting a GPE entity type. In an embodiment, named-entity disambiguation service 550 can populate a when attribute of the 5-tuple representation with named-entities comprising unique identities and named-entity tags denoting a Date entity type.

While embodiments of extraction component 140 can use sentences as logical units for extracting NPI events, a given sentence can lack information relating to one or more attributes of a particular NPI event in some instances. For example, the sentence corresponding the evidence of the NPI event shown in FIG. 3 is shown as comprising information relating to the what attribute, the value attribute, the when attribute, and the restriction attribute of the 5-tuple representation defining that NPI event. However, FIG. 3 shows information relating to the where attribute of that 5-tuple representation as being available in the document title. The example of FIG. 3 illustrates that in some instances information relating to various attributes corresponding to an NPI event can be available in different portions of a document from which the NPI event can be extracted.

For example, information relating to a subset of attributes corresponding to an NPI event can be available in a given sentence of a document while other attributes corresponding to that NPI event can be available in sentences of the document that are proximate to the given sentence, a paragraph header associated with the given sentence, and/or a title of the document. In an embodiment, extraction component 140 can comprise a heuristic-based relation detection algorithm to facilitate locating and/or extracting attributes corresponding to an NPI event that can be distributed in different portions of a document from which the NPI event was extracted. To that end, the heuristic-based relation detection algorithm can associate a Date entity type, a GPE entity type, and/or a PoS entity type extracted from a current document to one or more sentences of the current document.

Value extraction service 560 can evaluate textual data comprising sentences to extract information that further qualify event types denoted by classifications assigned to the sentences by event type service 520. In an embodiment, value extraction service 560 can use a rule-based matching algorithm (e.g., Spacy's rule-based matching algorithm) to examine patterns of constituent elements that can be reflected as tokens, phrases, and/or dependencies in an input sentence. By way of example, a rule-based token matcher can facilitate matching sequences based on lists of token descriptions, a phrase matcher can efficiently match large terminology lists, and/or a dependency matcher can match patterns within the dependency parse expressed using semgrex operators. A subset of manually labeled data with values can be used to develop one or more matching rules. In an embodiment, the rule-based matching algorithm can output values that can populate value attributes of 5-tuple representations that define NPI events extracted from the sentences. In an embodiment, the rule-based algorithm can output the values independent of results obtained from, at least, one of named-entity recognition service 540 and/or named-entity disambiguation service 550. For example, an input of the rule-based matching algorithm can receive the following sentence: "On 13 March, it was announced at an official press conference that a four-week ban on public gatherings of more than 100." The rule-based matching algorithm can also receive as input a classification that event type service 520 assigned to the sentence that denotes "restrictions on gatherings" event type as the particular event type. A taxonomy of NPI dataset 445 can identify "maximum number of people in social gatherings allowed by the government" as being the value attribute associated with the "restrictions on gatherings" event type. As such, the rule-based matching algorithm can extract and/or output the value "100" from the sentence of this example absent any information related to named-entities, such as named-entity tags that named-entity recognition service 540 can assign to named-entities or unique identities that named-entity disambiguation service 550 assigns to such named-entities.

In an embodiment, the parse-based rule algorithm can output the values using a result obtained from one or more of named-entity recognition service 540 and/or named-entity disambiguation service 550. For example, an input of the parse-based rule algorithm can receive the following sentence: "On 1 April, the Government of USA suspended flights from New York to Texas." The parse-based rule algorithm can also receive as input a classification that event type service 520 assigned to the sentence that denotes "domestic flight restrictions" event type as the particular event type. A taxonomy of NPI dataset 445 can identify "name of the state where the passenger is arriving from" as being the value attribute associated with the "domestic flight restrictions" event type. With the sentence including the names of two states (e.g., New York and Texas), the parse-based algorithm can use information relating to named-entities from named-entity recognition service 540 and/or named-entity disambiguation service 550 as input to facilitate identifying which state that passengers are arriving from. Absent such information, a likelihood that the parse-based algorithm identifies the correct state (e.g., New York) can be reduced.

With reference to FIG. 4, change detection component 150 can evaluate candidate NPI events extracted by extraction component 140 for inclusion in NPI dataset 445. To that end, change detection component 150 can evaluate an attribute of a given NPI candidate event to derive a similarity metric. The attributes can include one or more attributes of a 5-tuple representation that defines the given NPI candidate event. The similarity metric can include a syntactic similarity metric (e.g., a Levenshtein norm metric and/or other syntactic similarity metrics), a semantic similarity metric (e.g., an event attribute matching metric and/or other semantic similarity metrics), or a combination thereof. Using the similarity metric, change detection component 150 can determine whether the given NPI candidate event can be added to NPI dataset 445 as a new NPI event, update an existing NPI event stored in NPI dataset 445, or be discarded as duplicative.

In an embodiment, change detection component 150 can exclude a particular candidate NPI event from inclusion in NPI dataset 445 when a corresponding similarity metric indicates that the particular candidate NPI event is duplicative. For example, the corresponding similarity metric can indicate that a given sentence (e.g., evidence) from which the particular candidate NPI event was extracted remains unchanged from a previous time that crawler component 170 obtained a document comprising the given sentence from heterogeneous data sources 420. As another example, the corresponding similarity metric can indicate that a wording of the given sentence changed from the previous time that crawler component 170 obtained the document but a meaning of the given sentence has remained unchanged. In this example, change detection component 150 can flag the particular candidate NPI event as a possible duplicate NPI event for verification by validation component 432. In an embodiment, crawler component 170 can assign globally unique identifiers to different crawls of heterogeneous data sources 420. In an embodiment, the globally unique identifiers and/or dates of the different crawls can be stored in association with the NPI events to facilitate comparison of NPI events extracted from documents retrieved during different crawls.

Machine learning framework 400 can further include a curator tool 430 that can comprise a database 440 storing NPI dataset 445, a curation component 160, and/or a validation component 432. Curator tool 430 generally facilitates validating the accuracy, veracity, and/or completeness of NPI events output by event processing pipeline 410 to ensure data quality of NPI dataset 445. Curation component 160 can select a subset of NPI events stored in NPI dataset 445 for validation using a machine learning model and/or confidence scores associated with the NPI events. In an embodiment, the machine learning model can use a defined threshold to populate the subset of NPI events with NPI events by comparing respective confidence scores of the NPI events with the defined threshold.

In an embodiment, a confidence score associated with a given NPI event can comprise one or more confidence scores obtained from individual NLP components of event processing pipeline 410 that can be involved in extracting attributes of the given NPI event. Example NLP components of event processing pipeline 410 can include, but are not limited to, a sentence boundary detection algorithm of pre-processing service 510, a first classification model of event type service 520, a second classification model of restriction type service 530, a named-entity recognition algorithm of named-entity recognition service 540, a normalization algorithm of named-entity disambiguation service 550, and/or a parse-based rule algorithm of value extraction service 560. A given confidence score of the one or more confidence scores obtained from individual NLP components of event processing pipeline 410 can correspond to a particular attribute (e.g., a what attribute, a value attribute, a where attribute, a when attribute, and/or a restriction attribute) of the given NPI event. In an embodiment, a confidence score associated with a given NPI event can comprise an overall confidence score that corresponds to the given NPI event at large.

Validation component 432 can validate the accuracy, veracity, and/or completeness of NPI events within a subset of NPI events selected by curation component 160. In an embodiment, validation component 432 can validate the accuracy of an NPI event within the subset of NPI events by comparing an entry populating an attribute of the NPI event with an evidence associated with the NPI event. In an embodiment, validation component 432 can validate the veracity of the NPI event by comparing an entry populating an attribute of the NPI event with citation data associated with the NPI event. In an embodiment, validation component 432 can validate the completeness of the NPI event by evaluating a 5-tuple representation defining the NPI event to identify attributes of the 5-tuple representation that lack entries. In an embodiment, validation component 432 can populate an attribute of the 5-tuple representation identified as lacking an entry with information derived from an evidence associated with the NPI event. In an embodiment, validation component 432 can generate change data indicative of modifications to a given NPI that validation component made while validating the accuracy, veracity, and/or completeness of that NPI event. In an embodiment, curation component 160 can iteratively train the machine learning model using change data generated by validation component 432. In an embodiment, validation component 432 can comprise a human-in-the-loop component that facilitates validating the subset of NPI events selected by curation component 160.

Machine learning framework 400 can further include a post-processing service 450 that can process queries related to NPIs and populate responses to such queries using NPI dataset 445. By way of example, post-processing service 450 can process a query requesting NPI data for a particular geographical region during a specific time period. In this example, post-processing service 450 can access NPI dataset 445 to identify NPI events that comprise what attributes and when attributes that correspond to the particular geographical region and specific time period, respectively. Post-processing service 450 can populate a response to the query using the identified NPI events stored in NPI dataset 445. In an embodiment, the response can comprise a chart, a map, a histogram, and/or other visualizations of NPI data provided by the identified NPI events.

Figure 6:
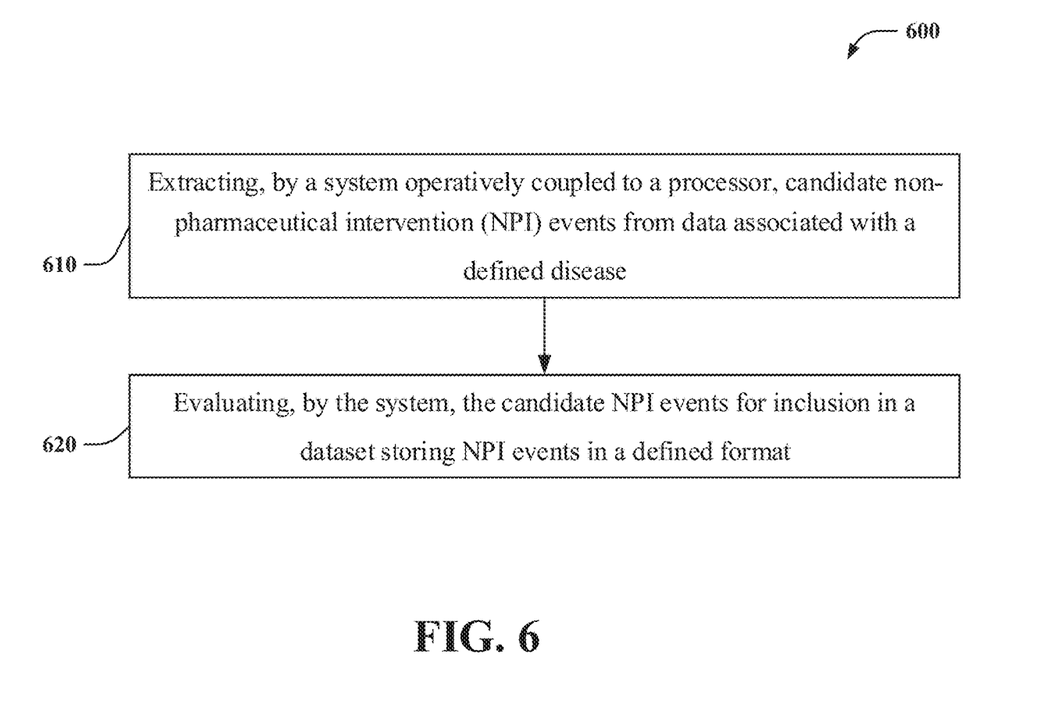
FIG. 6 illustrates a flow diagram of an example, non-limiting computer-implemented method of facilitating AI-assisted curation of NPI data from heterogeneous data sources, in accordance with one or more embodiments described herein.

FIG. 6 illustrates a flow diagram of an example, non-limiting computer-implemented method 600 of facilitating AI-assisted curation of NPI data from heterogeneous data sources, in accordance with one or more embodiments described herein. Repetitive description of like elements employed in other embodiments described herein is omitted for sake of brevity. At 610, the computer-implemented method 600 can comprise extracting, by a system operatively coupled to a processor (e.g., with extraction component 140), candidate NPI events from data associated with a defined disease. In an embodiment, the data can be textual data of documents associated with the defined disease. In an embodiment, extracting the candidate NPI events comprise using, by the system, a NPL model to extract the candidate NPI events from the textual data. At 620, the computer-implemented method 600 can comprise evaluating, by the system (e.g., with change detection component 150), the candidate NPI events for inclusion in a dataset (e.g., NPI dataset 345) storing NPI events in a defined format. In an embodiment, the computer-implemented method 600 can further comprise selecting, by the system (e.g., with curation component 160), a subset of NPI events stored in the dataset for validation using a machine learning model and confidence scores associated with the NPI events.

Figure 7:
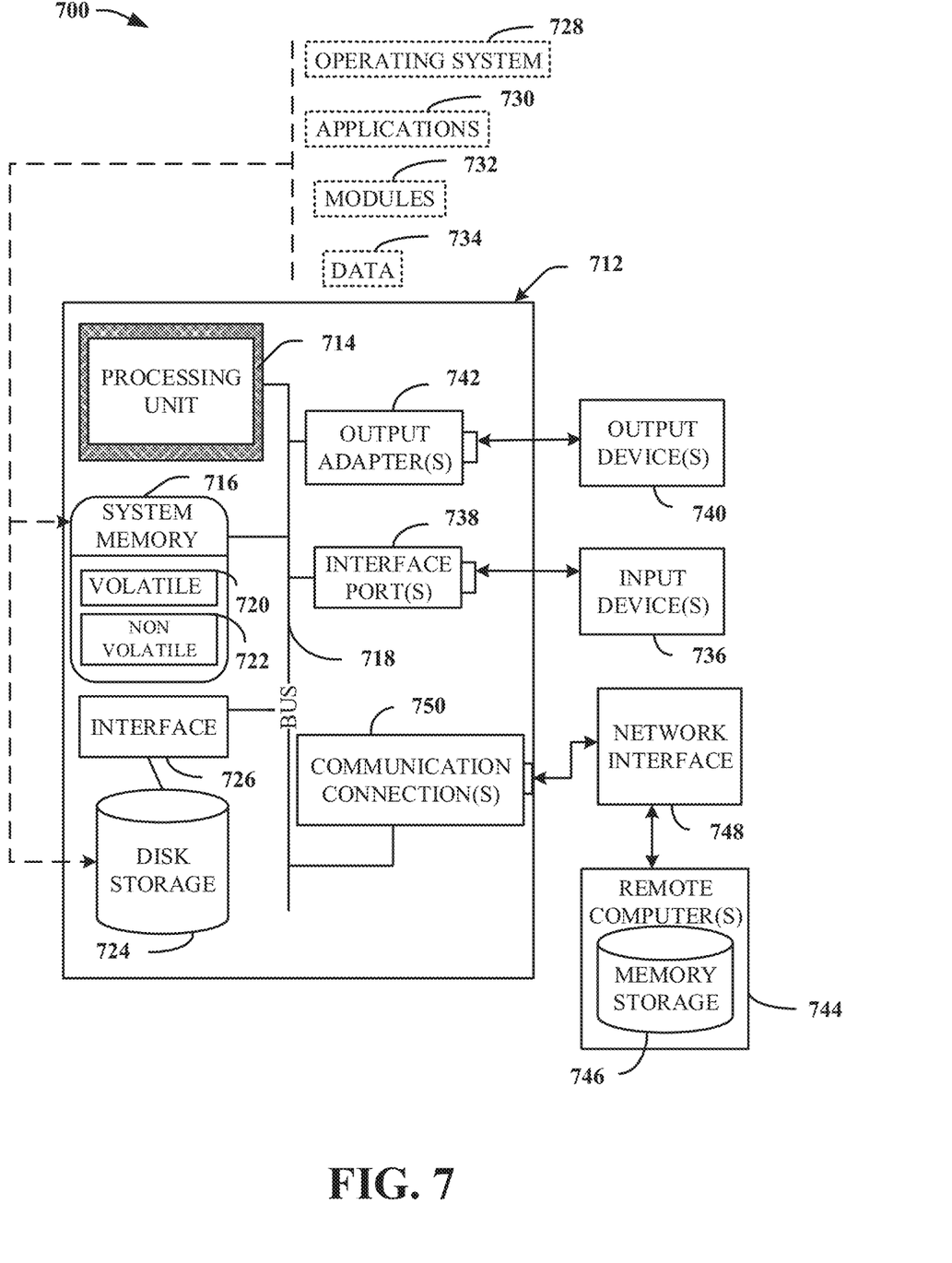
FIG. 7 illustrates a block diagram of an example, non-limiting operating environment in which one or more embodiments described herein can be facilitated.

In order to provide a context for the various aspects of the disclosed subject matter, FIG. 7 as well as the following discussion are intended to provide a general description of a suitable environment in which the various aspects of the disclosed subject matter can be implemented. FIG. 7 illustrates a suitable operating environment 700 for implementing various aspects of this disclosure can also include a computer 712. The computer 712 can also include a processing unit 714, a system memory 716, and a system bus 718. The system bus 718 couples system components including, but not limited to, the system memory 716 to the processing unit 714. The processing unit 714 can be any of various available processors. Dual microprocessors and other multiprocessor architectures also can be employed as the processing unit 714. The system bus 718 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire (IEEE 1094), and Small Computer Systems Interface (SCSI). The system memory 716 can also include volatile memory 720 and nonvolatile memory 722. The basic input/output system (BIOS), containing the basic routines to transfer information between elements within the computer 712, such as during start-up, is stored in nonvolatile memory 722. By way of illustration, and not limitation, nonvolatile memory 722 can include read only memory (ROM), programmable ROM (PROM), electrically programmable ROM (EPROM), electrically erasable programmable ROM (EEPROM), flash memory, or nonvolatile random-access memory (RAM) (e.g., ferroelectric RAM (FeRAM). Volatile memory 720 can also include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 712 can also include removable/non-removable, volatile/non-volatile computer storage media. FIG. 7 illustrates, for example, a disk storage 724. Disk storage 724 can also include, but is not limited to, devices like a magnetic disk drive, floppy disk drive, tape drive, Jaz drive, Zip drive, LS-100 drive, flash memory card, or memory stick. The disk storage 724 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 724 to the system bus 718, a removable or non-removable interface is typically used, such as interface 726. FIG. 7 also depicts software that acts as an intermediary between users and the basic computer resources described in the suitable operating environment 700. Such software can also include, for example, an operating system 728. Operating system 728, which can be stored on disk storage 724, acts to control and allocate resources of the computer 712. System applications 730 take advantage of the management of resources by operating system 728 through program modules 732 and program data 734, e.g., stored either in system memory 716 or on disk storage 724. It is to be appreciated that this disclosure can be implemented with various operating systems or combinations of operating systems. A user enters commands or information into the computer 712 through input device(s) 736. Input devices 736 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 714 through the system bus 718 via interface port(s) 738. Interface port(s) 738 include, for example, a serial port, a parallel port, a game port, and a universal serial bus (USB). Output device(s) 740 use some of the same type of ports as input device(s) 736. Thus, for example, a USB port can be used to provide input to computer 712, and to output information from computer 712 to an output device 740. Output adapter 742 is provided to illustrate that there are some output devices 740 like monitors, speakers, and printers, among other output devices 740, which require special adapters. The output adapters 742 include, by way of illustration and not limitation, video and sound cards that provide a means of connection between the output device 740 and the system bus 718. It can be noted that other devices and/or systems of devices provide both input and output capabilities such as remote computer(s) 744.

Computer 712 can operate in a networked environment using logical connections to one or more remote computers, such as remote computer(s) 744. The remote computer(s) 744 can be a computer, a server, a router, a network PC, a workstation, a microprocessor-based appliance, a peer device or other common network node and the like, and typically can also include many or the elements described relative to computer 712. For purposes of brevity, only a memory storage device 746 is illustrated with remote computer(s) 744. Remote computer(s) 744 is logically connected to computer 712 through a network interface 748 and then physically connected via communication connection 750. Network interface 748 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). Communication connection(s) 750 refers to the hardware/software employed to connect the network interface 748 to the system bus 718. While communication connection 750 is shown for illustrative clarity inside computer 712, it can also be external to computer 712. The hardware/software for connection to the network interface 748 can also include, for exemplary purposes only, internal and external technologies such as, modems including regular telephone grade modems, cable modems and DSL modems, ISDN adapters, and Ethernet cards.

The present invention may be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices. For example, in one or more embodiments, computer executable components can be executed from memory that can include or be comprised of one or more distributed memory units. As used herein, the term "memory" and "memory unit" are interchangeable. Further, one or more embodiments described herein can execute code of the computer executable components in a distributed manner, e.g., multiple processors combining or working cooperatively to execute code from one or more distributed memory units. As used herein, the term "memory" can encompass a single memory or memory unit at one location or multiple memories or memory units at one or more locations.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
a processor that executes the following computer-executable components stored in memory:
an extraction component that:
extracts candidate non-pharmaceutical intervention (NPI) events from unstructured data in heterogeneous data sources associated with a defined disease, and
converts the candidate non-pharmaceutical intervention (NPI) events into structured candidate NPI events in a defined format comprising a tuple representation, wherein the tuple is a 5-tuple representation comprises:
a what attribute that identifies a type of NPI of an NPI event,
a value attribute that identifies a subcategory of the type of NPI,
a where attribute that identifies a location of occurrence of the NPI event,
a when attribute that identifies a time period of occurrence of the NPI event, and
a restriction attribute that identifies whether the NPI event was associated with an imposition or a lifting of the type of NPI; and
a change detection component that evaluates the structured candidate NPI events for inclusion in a dataset storing NPI events in the defined format.

2. The system of claim 1, wherein the tuple is a 6-tuple representation that further comprises an an enforcement attribute that identifies a enforcing body that enforces the type of NPI.

3. The system of claim 1, wherein the unstructured data comprises textual data of documents associated with the defined disease, and wherein the extraction component extracts the candidate NPI events from the textual data using a natural language processing (NPL) model.

4. The system of claim 3, wherein the extraction component extracts the candidate NPI events using a sentence boundary detection algorithm to partition the textual data of the documents into sentences.

5. The system of claim 1, wherein the change detection component evaluates the structured candidate NPI events for inclusion in the dataset using similarity metrics derived from attributes of the structured candidate NPI events.

6. The system of claim 1, wherein the change detection component excludes a particular structured candidate NPI event of the structured candidate NPI events from inclusion in the dataset when a corresponding similarity metric indicates the particular structured candidate NPI event is duplicative.

7. The system of claim 1, wherein the extraction component further categorizes a particular candidate NPI event among the candidate NPI events by assigning the type of NPI from a set of types of NPIs to a given sentence of documents associated with the defined disease using a sentence classification model.

8. The system of claim 1, wherein the extraction component further identifies attributes of the candidate NPI events by evaluating textual data of documents associated with the defined disease using a named-entity recognition service, a named-entity disambiguation service, or a combination thereof.

9. The system of claim 1, wherein the extraction component further extracts values for attributes of the candidate NPI events by evaluating textual data of documents associated with the defined disease using a parse-based rule algorithm.

10. The system of claim 9, wherein the parse-based rule algorithm outputs the values for the attributes of the candidate NPI events using a result obtained from one or more of a named-entity recognition service and a named-entity disambiguation service.

11. The system of claim 9, wherein the parse-based rule algorithm outputs the values for the attributes of the candidate NPI events independent of results obtained from a named-entity recognition service and a named-entity disambiguation service.

12. The system of claim 1 further comprising:
a curation component that selects a subset of NPI events stored in the dataset for validation using a machine learning model and confidence scores associated with the NPI events.

13. The system of claim 12, wherein the curation component iteratively trains the machine learning model using change data generated from validation of the subset of the NPI events stored in the dataset.

14. The system of claim 1, further comprising:
a crawler component that periodically crawls the heterogeneous data sources to retrieve the unstructured data associated with the defined disease.

15. A computer-implemented method, comprising:
extracting, by a system operatively coupled to a processor, candidate non-pharmaceutical intervention (NPI) events from unstructured data in heterogeneous data sources associated with a defined disease;
converting, by the system, the candidate non-pharmaceutical intervention (NPI) events into structured candidate NPI events in a defined format comprising a tuple representation, wherein the tuple is a 5-tuple representation comprises:
a what attribute that identifies a type of NPI of an NPI event,
a value attribute that identifies a subcategory of the type of NPI,
a where attribute that identifies a location of occurrence of the NPI event,
a when attribute that identifies a time period of occurrence of the NPI event, and
a restriction attribute that identifies whether the NPI event was associated with an imposition or a lifting of the type of NPI; and
evaluating, by the system, the structured candidate NPI events for inclusion in a dataset storing NPI events in the defined format.

16. The computer-implemented method of claim 15, wherein the unstructured data comprises textual data of documents associated with the defined disease, and wherein extracting the candidate NPI events comprises:
using, by the system, a natural language processing (NPL) model to extract the candidate NPI events from the textual data.

17. The computer-implemented method of claim 15, further comprising:
selecting, by the system, a subset of NPI events stored in the dataset for validation using a machine learning model and confidence scores associated with the NPI events.

18. A computer program product comprising a computer readable storage medium having program instructions embodied therewith, the program instructions executable by a processor to cause the processor to:
extract, by the processor, candidate non-pharmaceutical intervention (NPI) events from unstructured data in heterogeneous data sources associated with a defined disease;
convert, by the processor, the candidate non-pharmaceutical intervention (NPI) events into structured candidate NPI events in a defined format comprising a tuple representation, wherein the tuple is a 5-tuple representation comprises:
a what attribute that identifies a type of NPI of an NPI event,
a value attribute that identifies a subcategory of the type of NPI,
a where attribute that identifies a location of occurrence of the NPI event,
a when attribute that identifies a time period of occurrence of the NPI event, and
a restriction attribute that identifies whether the NPI event was associated with an imposition or a lifting of the type of NPI; and
evaluate, by the processor, the structured candidate NPI events for inclusion in a dataset storing NPI events in the defined format.

19. The computer program product of claim 18, wherein the unstructured data comprises textual data of documents associated with the defined disease, and wherein the program instructions further cause the processor to:
use, by the processor, a natural language processing (NPL) model to extract the candidate NPI events from the textual data.

20. The computer program product of claim 18, wherein the program instructions further cause the processor to:
select, by the processor, a subset of NPI events stored in the dataset for validation using a machine learning model and confidence scores associated with the NPI events.

* * * * *